(12) United States Patent
Takada et al.

(10) Patent No.: US 9,160,132 B2
(45) Date of Patent: Oct. 13, 2015

(54) LASER APPARATUS, LIGHT THERAPY APPARATUS, EXPOSURE APPARATUS, DEVICE MANUFACTURING METHOD, AND OBJECT INSPECTION APPARATUS

(75) Inventors: Yasutoshi Takada, Kawasaki (JP); Akira Tokuhisa, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 132 days.

(21) Appl. No.: 13/029,806

(22) Filed: Feb. 17, 2011

(65) Prior Publication Data

US 2011/0143286 A1    Jun. 16, 2011

Related U.S. Application Data

(63) Continuation of application No. PCT/JP2009/003916, filed on Aug. 18, 2009.

(30) Foreign Application Priority Data

Aug. 26, 2008  (JP) ................................. 2008-217317

(51) Int. Cl.
*G03B 27/42* (2006.01)
*H01S 3/067* (2006.01)
(Continued)

(52) U.S. Cl.
CPC .............. *H01S 3/06754* (2013.01); *A61B 18/22* (2013.01); *A61F 9/00804* (2013.01);
(Continued)

(58) Field of Classification Search
CPC ........... B23K 26/0639; B23K 26/0643; B23K 26/0648; B23K 26/0665; G03F 7/70058; G03F 7/70575; G03F 7/70566; G03F 7/70025; G03F 7/70983; H01S 3/13; H01S 3/1301; H01S 3/06754; A61F 9/00804; A61F 9/00819; A61B 18/22
USPC ........... 355/53, 67, 69, 71; 250/492.2, 292.22
See application file for complete search history.

(56) References Cited

U.S. PATENT DOCUMENTS

2002/0001124 A1*  1/2002  Kinoshita et al. .......... 359/337.1
2002/0027703 A1   3/2002  Kinoshita et al.
(Continued)

FOREIGN PATENT DOCUMENTS

CN    1232192 A    10/1999
CN    1614496 A    5/2005
(Continued)

OTHER PUBLICATIONS

International Search Report for corresponding International Patent Application No. PCT/JP2009/003916, mailed on Sep. 15, 2009 (w/ English translation).
(Continued)

*Primary Examiner* — Mesfin T Asfaw
(74) *Attorney, Agent, or Firm* — Oliff PLC

(57) ABSTRACT

The present invention greatly reduces the likelihood that fiber fusion will occur. A laser apparatus comprises an excitation light source and an optical amplifier unit, which optically amplifies by receiving excitation light that is output from the excitation light source and that transits an optical fiber. A monitor unit monitors the power level of the excitation light transmitted from the excitation light source to the optical amplifier unit side via the optical fiber. At the initial start of the output of the excitation light from the excitation light source, once the excitation light is being output at the prescribed power level by the excitation light source, the control unit performs control such that the excitation light at a power level higher than the prescribed power level is output if the power level monitored by the monitor unit is greater than or equal to a prescribed value when the excitation light at the prescribed power level is being output from the excitation light source and such that the output of the excitation light is stopped if the power level monitored by the monitor unit is less than the prescribed value when the excitation light at the prescribed power level is being output from the excitation light source.

8 Claims, 7 Drawing Sheets

(51) Int. Cl.
  *A61B 18/22* (2006.01)
  *A61F 9/008* (2006.01)
  *G03F 7/20* (2006.01)
  *A61B 18/20* (2006.01)
  *A61B 18/00* (2006.01)
  *H01S 3/00* (2006.01)
  *H01S 3/08* (2006.01)
  *H01S 3/13* (2006.01)
  *H01S 3/23* (2006.01)
  *H01S 3/30* (2006.01)

(52) U.S. Cl.
  CPC ........ *A61F9/00819* (2013.01); *G03F 7/70025* (2013.01); *G03F 7/70983* (2013.01); *A61B 18/20* (2013.01); *A61B 2018/00636* (2013.01); *A61F 2009/00844* (2013.01); *A61F 2009/00872* (2013.01); *H01S 3/0092* (2013.01); *H01S 3/08086* (2013.01); *H01S 3/1305* (2013.01); *H01S 3/2383* (2013.01); *H01S 3/302* (2013.01)

(56) References Cited

U.S. PATENT DOCUMENTS

| | | | | |
|---|---|---|---|---|
| 2002/0041429 A1* | 4/2002 | Sugaya et al. | ................ | 359/334 |
| 2002/0191171 A1* | 12/2002 | Nishi | ............................... | 355/67 |
| 2004/0012844 A1* | 1/2004 | Ohtsuki et al. | ............. | 359/341.1 |
| 2005/0164536 A1* | 7/2005 | Titchener | ...................... | 439/191 |
| 2005/0259314 A1 | 11/2005 | Tokuhisa et al. | | |

FOREIGN PATENT DOCUMENTS

| | | |
|---|---|---|
| CN | 1723594 A | 1/2006 |
| DE | 603 16 989 T2 | 7/2008 |
| EP | 0 944 189 A2 | 9/1999 |
| EP | 1 571 741 A1 | 9/2005 |
| JP | A-11-312848 | 11/1999 |
| JP | A-2003-318472 | 11/2003 |
| JP | B2-4009969 | 11/2007 |
| KR | A-1020050084198 | 8/2005 |
| WO | WO 2004/054050 A1 | 6/2004 |

OTHER PUBLICATIONS

Reasons of Rejection issued in Japanese Patent Application No. 2010-526520 dated Nov. 27, 2012 (w/ translation).
Sep. 15, 2009 Written Opinion of the International Searching Authority issued in Application No. PCT/JP2009/003916 (with translation).
May 27, 2014 Office Action issued in Taiwanese Patent Application No. 098128446 (with English translation).

* cited by examiner

LASER APPARATUS, LIGHT THERAPY APPARATUS, EXPOSURE APPARATUS, DEVICE MANUFACTURING METHOD, AND OBJECT INSPECTION APPARATUS

This is a continuation of PCT International Application No. PCT/JP2009/003916, filed on Aug. 18, 2009, which is hereby incorporated by reference. This application also claims the benefit of Japanese Patent Application No. 2008-217317, filed in Japan on Aug. 26, 2008, which is hereby incorporated by reference.

FIELD OF THE INVENTION

The present invention relates to a laser apparatus and to a light therapy apparatus, an exposure apparatus, a device manufacturing method, and an object inspection apparatus that uses the same.

BACKGROUND OF THE INVENTION

As an example of a laser apparatus, Patent Document 1 below discloses an ultraviolet light source that comprises: a laser light source, which generates a signal light that falls within a range extending from the infrared region to the visible region; an optical amplifier, which amplifies the signal light generated by the laser light source; a wavelength conversion optical system, which converts the wavelength of the signal light amplified by the optical amplifier to ultraviolet light and outputs such; and an excitation light source, which supplies excitation light to the optical amplifier.

In addition, Patent Document 1 below also discloses a light therapy apparatus, an exposure apparatus, and an object inspection apparatus wherein such an ultraviolet light source is used.

PRIOR ART LITERATURE

Patent Literature

Patent Document 1: Reissued Patent No. WO2004/054050

OVERVIEW OF THE INVENTION

Problems Solved by the Invention

In the laser apparatus as disclosed in Patent Document 1, it is preferable—in terms of convenience of transport and the like, increasing the degrees of freedom in the layout, avoiding the impact of heat from the excitation light source, and the like—to connect the excitation light source and the optical amplifier with an optical fiber along which a connecting part is provided.

In such a case, the optical fiber that connects the excitation light source and the optical amplifier is separated, at the time of transport, into an optical fiber on the optical amplifier side, one end of which is connected to the optical amplifier and the other end of which is left open, and an optical fiber on the excitation light source side, one end of which is connected to the excitation light source and the other end of which is left open. Thereby, the laser apparatus can be separated into the portion on the optical amplifier side and the portion on the excitation light source side, which facilitates transport and the like. Furthermore, when the laser apparatus is being installed, the other end of the optical fiber on the optical amplifier side and the other end of the optical fiber on the excitation light source side are connected by, for example, fusion splicing them together. As a result, along the optical fiber that connects the excitation light source and the optical amplifier of the laser apparatus, there is a connecting part that is formed by splicing.

Furthermore, this approach is advantageous not only during transport, but also when replacing, for example, the excitation light source of an existing laser apparatus with a new one; in such a case, the replacement is easy to perform by disconnecting, midway, the optical fibers that connect the excitation light source and the optical amplifier and then connecting the other end of the optical fiber on the optical amplifier side and the other end of the optical fiber on the excitation light source side, for example, by fusion splicing.

Incidentally, when performing the work to connect the optical fibers to one another, for example, by fusion splicing as discussed above, the connection state, for example, the spliced state, might be poor owing to mistakes deriving from the operator's low skill level, the failure of the fusion splicer, a poor operating environment, and the like. Furthermore, there is also a possibility that the operator may forget to connect the optical fibers together, for example, by fusion splicing as discussed above.

If the connection state, for example, the spliced state, between the optical fibers is poor or if the operator has forgotten to make the connection as discussed above, then the transmittance between the other end of the optical fiber on the optical amplifier side and the other end of the optical fiber on the excitation light source side is lower than the case wherein the two optical fibers are connected normally. Consequently, in this state, if high power light is generated from the excitation light source when the laser apparatus starts operation, a phenomenon (called fiber fusion), wherein light energy of high power from the excitation light source is absorbed in the portion of the optical fiber where the transmittance is low, will occur, causing the optical fiber to overheat and burn out.

In addition, even if the connection state, for example, the spliced state, between the optical fibers as discussed above is initially satisfactory, there is a possibility that the connection state, for example, the spliced state, will degrade over time or that the optical fibers will be damaged as a result of being subjected to a physical force and thereby broken. In such a case, too, fiber fusion occurs.

The present invention considers such circumstances, and it is an object of the present invention to provide a laser apparatus that can substantially reduce the likelihood of fiber fusion, and to provide a light therapy apparatus, an exposure apparatus, a device manufacturing method, and an object inspection apparatus that uses such a laser apparatus.

Means of Solving the Problems

Each of the aspects below is presented as a means to solve the aforementioned problems. A laser apparatus according to a first aspect of the present invention is a laser apparatus that comprises an excitation light source and an optical amplifier unit, which optically amplifies by receiving excitation light that is output from the excitation light source and that transits an optical fiber along which a connecting part is provided, and that outputs, as output light, light output from the optical amplifier unit and light based on that light, and comprises: a control unit, which controls the excitation light source; and a monitor unit, which monitors the power level of the excitation light transmitted from the excitation light source to the optical amplifier unit side via the optical fiber. In the present aspect of the present invention, at the initial start of the output of the excitation light from the excitation light source, once the excitation light is being output at the prescribed power level by the excitation light source, the control unit controls the excitation light source such that the excitation light at a power level higher than the prescribed power level is output by the excitation light source if the power level monitored by the monitor unit is greater than or equal to a prescribed value when the excitation light at the prescribed power level is being output from the excitation light source and such that the output of the excitation light by the excitation light source is stopped if the power level monitored by the monitor unit is less than the prescribed value when the excitation light at the prescribed power level is being output from the excitation light source.

A laser apparatus according to a second aspect of the present invention is a laser apparatus that comprises an excitation light source and an optical amplifier unit, which optically amplifies by receiving excitation light that is output from the excitation light source and that transits an optical fiber, and that outputs, as output light, light output from the optical amplifier unit and light based on that light, and comprises: a control unit, which controls the excitation light source; and a monitor unit, which monitors the power level of the excitation light transmitted from the excitation light source to the optical amplifier unit side via the optical fiber. In the present aspect of the present invention, when the excitation light source is outputting the excitation light, the control unit controls the excitation light source such that the output of the excitation light by the excitation light source is stopped if the power level monitored by the monitor unit is less than a prescribed value.

A light therapy apparatus according to a third aspect of the present invention comprises: a laser apparatus according to the first or second aspect of the present invention; and a radiation optical system, which guides and radiates the output light output from the laser apparatus to a therapy region.

An exposure apparatus according to a fourth aspect of the present invention is an exposure apparatus, which transfers a pattern of a mask to a photosensitive object, that comprises: a laser apparatus according to the first or second aspect of the present invention; an illumination optical system, which radiates output light output from the laser apparatus to the mask; and a projection optical system, which projects the light from the mask to the photosensitive object.

A device manufacturing method according to a fifth aspect of the present invention is a device manufacturing method, which includes a lithographic process, wherein the lithographic process uses an exposure apparatus according to the fourth aspect of the present invention to transfer a pattern of the mask to the photosensitive object.

An object inspection apparatus according to a sixth aspect of the present invention comprises: a laser apparatus according to the first or second aspect of the present invention; a support part, which supports an object to be inspected; a detector, which detects a projected image of the object to be inspected; an illumination optical system, which radiates output light output from the laser apparatus to the object to be inspected; and a projection optical system, which projects light from the object to be inspected to the detector.

Effects of the Invention

The present invention provides a laser apparatus that can substantially reduce the likelihood of fiber fusion, and provides a light therapy apparatus, an exposure apparatus, a device manufacturing method, and an object inspection apparatus that uses such a laser apparatus.

DETAILED DESCRIPTION OF THE PREFERRED EMBODIMENTS

A laser apparatus, a light therapy apparatus, an exposure apparatus, a device manufacturing method, and an object inspection apparatus according to the present invention will now be explained, referencing the drawings.

First Embodiment

Figure 1:
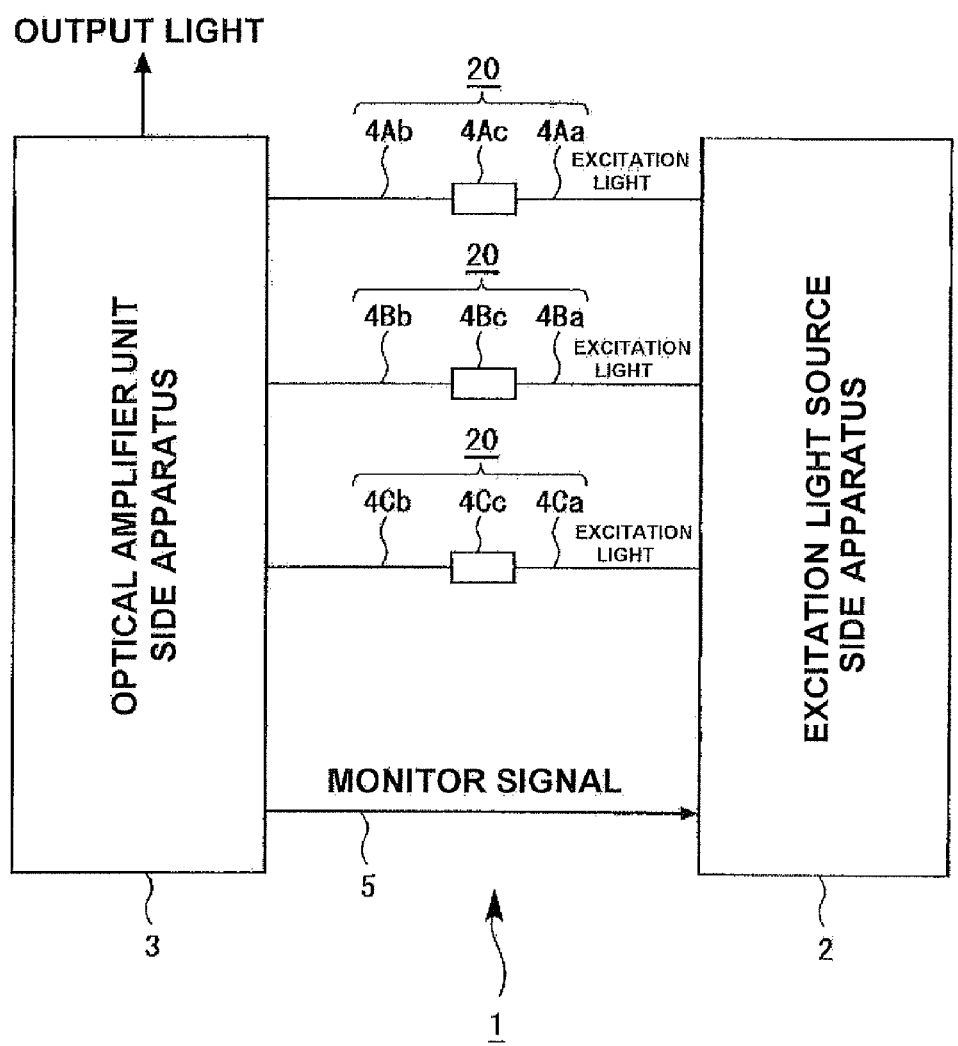
FIG. 1 is a schematic block diagram that shows a laser apparatus according to first embodiment of the present invention.

FIG. 1 is a schematic block diagram that shows a laser apparatus 1 according to a first embodiment of the present invention. The laser apparatus 1 according to the present embodiment comprises an excitation light source side apparatus 2, an optical amplifier unit side apparatus 3, optical fibers 4Aa, 4Ab, 4Ba, 4Bb, 4Ca, 4Cb, which are for excitation lights and connect the apparatuses 2, 3, and an electrical signal line 5 for monitor signals.

The optical fiber 4A comprises optical fibers 4Aa, 4Ab, one end of each of which are connected together by a connecting part 4Ac, which the optical fiber 4A comprises midway. The other end of the optical fiber 4Aa is connected to the excitation light source side apparatus 2, and the other end of the optical fiber 4Ab is connected to the optical amplifier unit side apparatus 3. Likewise, the optical fiber 4B consists of optical fibers 4Ba, 4Bb, one end of each of which are connected together by a connecting part 4Bc, which the optical fiber 4B comprises midway. The other end of the optical fiber 4Ba is connected to the excitation light source side apparatus 2, and the other end of the optical fiber 4Bb is connected to the optical amplifier unit side apparatus 3. Likewise, the optical fiber 4C consists of optical fibers 4Ca, 4Cb, one end of each of which are connected by a connecting part 4Cc, which the optical fiber 4C comprises midway. The other end of the optical fiber 4Ca is connected to the excitation light source side apparatus 2, and the other end of the optical fiber 4Cb is connected to the optical amplifier unit side apparatus 3. In the present embodiment, the connections of these optical fibers 4Aa, 4Ab, 4Ba, 4Bb, 4Ca, 4Cb are performed entirely by fusion splicing, and the connecting parts 4Ac, 4Bc, 4Cc are spliced parts. In the present invention, the connection of these optical fibers 4Aa, 4Ab, 4Ba, 4Bb, 4Ca, 4Cb is naturally not limited to fusion splicing and the connecting parts 4Ac, 4Bc, 4Cc are not limited to spliced parts.

The laser apparatus 1 according to the present embodiment is transported in the state wherein the optical fibers 4Aa, 4Ba, 4Ca and the optical fibers 4Ab, 4Bb, 4Cb are separated from one another and not connected by the connecting parts 4Ac, 4Bc, 4Cc. Furthermore, during installation and, for example, after replacing only the excitation light source side apparatus 2, the optical fibers 4Aa, 4Ba, 4Ca and the optical fibers 4Ab, 4Bb, 4Cb are connected by the connecting parts 4Ac, 4Bc, 4Cc, respectively.

Figure 2:
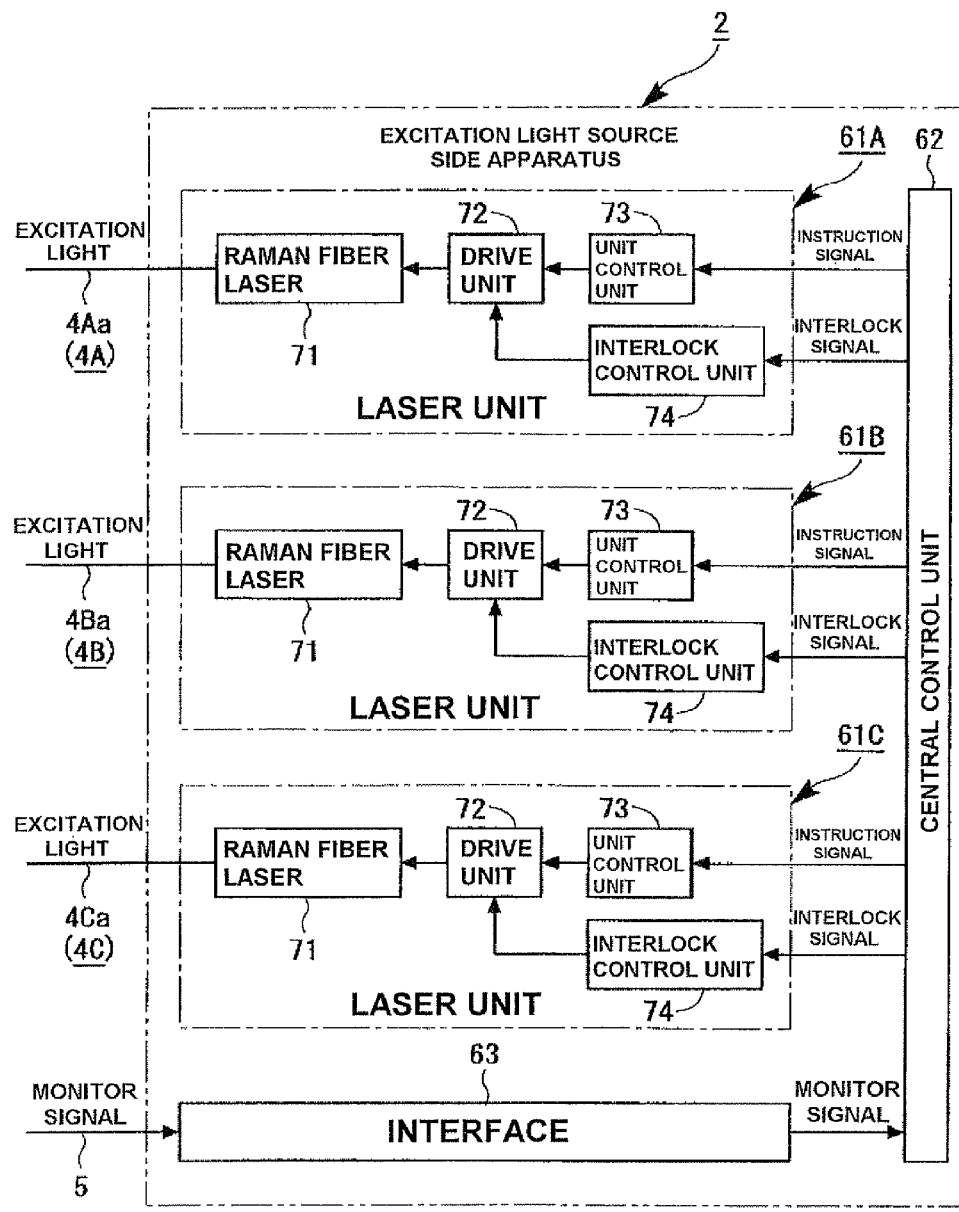
FIG. 2 is a schematic block diagram that shows an excitation light source side apparatus in FIG. 1.
Figure 3:
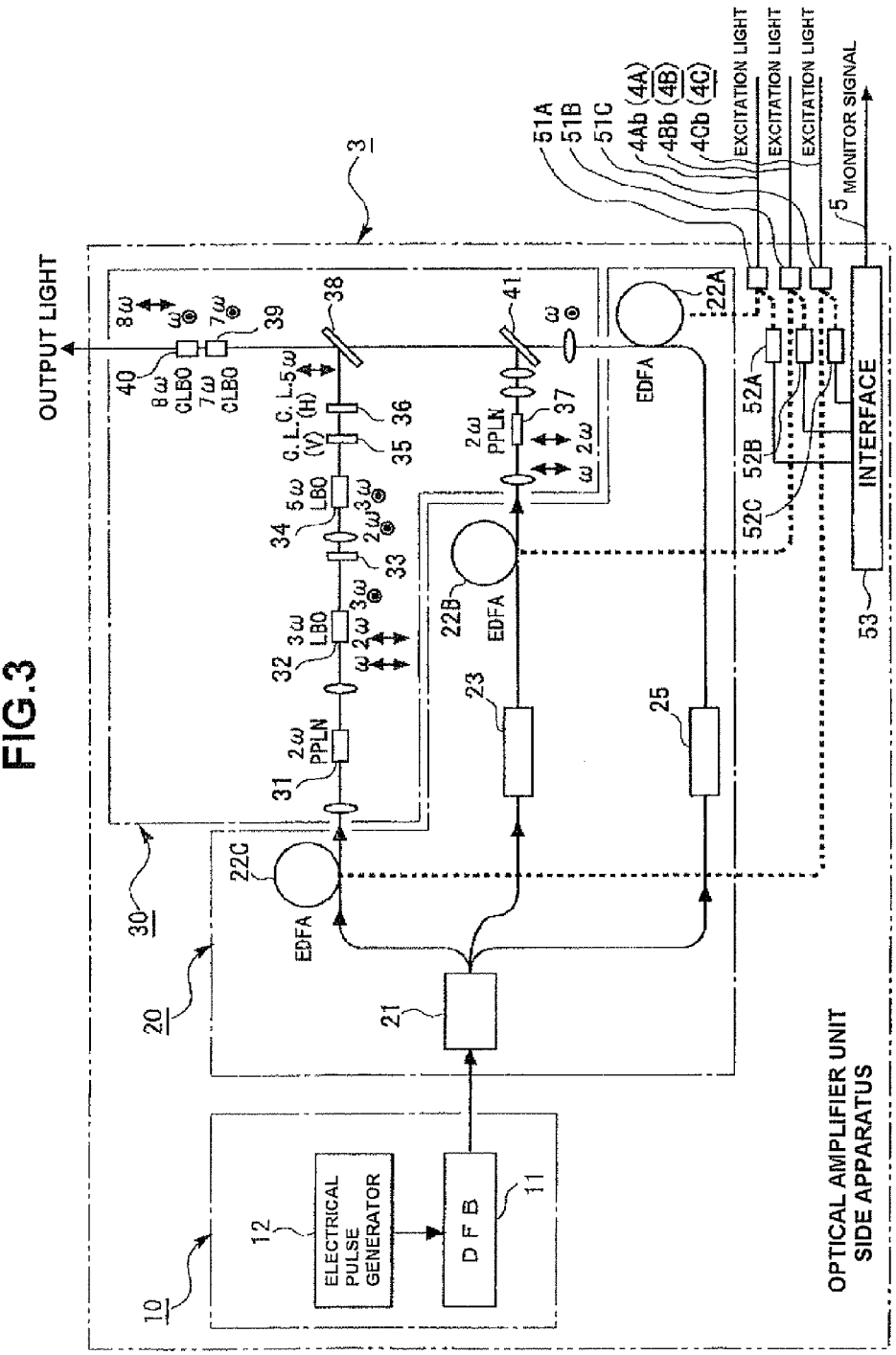
FIG. 3 is a schematic block diagram that shows an optical amplifier unit side apparatus in FIG. 1.

FIG. 2 is a schematic block diagram that shows the excitation light source side apparatus 2 in FIG. 1. FIG. 3 is a schematic block diagram that shows the optical amplifier unit side apparatus 3 in FIG. 1.

As shown in FIG. 2, the optical fibers 4Aa, 4Ba, 4Ca are connected to Raman fiber lasers 71 of laser units 61A, 61B, 61C of the excitation light source side apparatus 2. In addition, as shown in FIG. 3, the optical fibers 4Ab, 4Bb, 4Cb are connected to couplers 51A, 51B, 51C of the optical amplifier unit side apparatus 3. Thereby, excitation lights generated by the Raman fiber lasers 71 of the laser units 61A, 61B, 61C of the excitation light source side apparatus 2 are transmitted by the optical fibers 4A, 4B, 4C and reach the couplers 51A, 51B, 51C, respectively.

First, the optical amplifier unit side apparatus 3 will be explained, referencing FIG. 3. The excitation light source side apparatus 2 will be discussed in detail later.

The excitation light that reaches the coupler 51A is split in two with a prescribed ratio; the majority portion thereof is supplied to an EDFA (erbium doped fiber optical amplifier) 22A, which serves as an optical amplifier of an optical amplifier unit 20, and the remaining portion is supplied to a detector 52A, such as a photodiode, which serves as a monitor unit that monitors the power level of that excitation light. The detector 52A outputs a monitor signal, which indicates the power level of that excitation light, to an interface 53.

The excitation light that reaches the coupler 51B is split in two with a prescribed ratio; the majority portion thereof is supplied to an EDFA 22B, which serves as an optical amplifier of the optical amplifier unit 20, and the remaining portion is supplied to a detector 52B, such as a photodiode, which serves as a monitor unit that monitors the power level thereof. The detector 52B outputs a monitor signal, which indicates the power level of that excitation light, to the interface 53.

The excitation light that reaches the coupler 51C is split in two with a prescribed ratio; the majority portion thereof is supplied to an EDFA 22C, which serves as an optical amplifier of the optical amplifier unit 20, and the remaining portion is supplied to a detector 52C, such as a photodiode, which serves as a monitor unit that monitors the power level thereof. The detector 52C outputs a monitor signal, which indicates the power level of that excitation light, to the interface 53.

Furthermore, the couplers 51A, 51B, 51C and the detectors 52A, 52B, 52C do not have to be disposed at the position discussed above as long as they are disposed at a position at which they can directly or indirectly monitor the power levels of the excitation lights discussed above. For example, the couplers 51A, 51B, 51C and the detectors 52A, 52B, 52C ran also be provided along the EDFAs 22A, 22B, 22C.

The interface 53 converts the monitor signals from the detectors 52A, 52B, 52C to a prescribed signal format and transmits such to the excitation light source side apparatus 2 via the signal line 5.

As shown in FIG. 3, in addition to the couplers 51A, 51B, 51C and the detectors 52A, 52B, 52C discussed above, the optical amplifier unit side apparatus 3 comprises a seed light generating unit 10, which is configured as a laser light source, the optical amplifier unit 20, which optically amplifies seed light generated by the seed light generating unit 10, and a wavelength converting part 30, which converts the wavelength of the light optically amplified by the optical amplifier unit 20. In the present embodiment, the output light of the wavelength converting part 30 of the optical amplifier unit side apparatus 3 is the output light of the laser apparatus 1. In the present embodiment, ultraviolet pulsed light with a wavelength of 193.4 nm is output as the output light. Naturally, depending on the application, the wavelength converting part 30 may be removed and the output light of the optical amplifier unit 20 may serve as the output light of the laser apparatus 1.

In the present embodiment, the seed light generating unit 10 comprises a DFB (distributed feedback) semiconductor laser 11 and an electrical pulse generator 12. For example, an InGaAsP DFB semiconductor laser with an oscillation wavelength of 1.547 μm is used as the DFB semiconductor laser 11. The electrical pulse generator 12 is a driver that controls the operation of the DFB semiconductor laser 11, wherein, for example, the driver pulses a drive signal with a pulse width of approximately 1 ns and a repetition frequency f equal to several tens to several hundreds of kilohertz and supplies such to the DFB semiconductor laser 11. Thereby, the DFB semiconductor laser 11 outputs pulsed seed light (i.e., signal light, light of the fundamental wave) with a peak power of approximately 10 mW to the optical amplifier unit 20.

The optical amplifier unit 20 comprises: a coupler 21, which splits the seed light from the seed light generating unit 10 into three parts; the first EDFA 22C, which serves as an optical amplifier that amplifies one of the lights resulting from the split; a retarder 23, which retards another one of the lights resulting from the split; the second EDFA 22B, which serves as an optical amplifier that amplifies the light retarded by the retarder 23; a retarder 25, which retards the one remaining light resulting from the split; and the third EDFA 22A, which serves as an optical amplifier that amplifies the light retarded by the retarder 25. The EDFAs 22A, 22B, 22C receive and optically amplify the excitation lights discussed above.

Next, the wavelength converting part 30 will be explained. In FIG. 3, elements indicated by elliptical shapes are collimator lenses, condenser lenses, and the like, and explanations thereof are omitted. In addition, in FIG. 3, P polarized lights are indicated by arrows, and S polarized lights are indicated by a dot in a circle; furthermore, the fundamental wave is denoted as ω and the nth harmonic wave is denoted as nω.

As shown in FIG. 3, the fundamental wave of the P polarized light amplified by the first EDFA 22C enters a first second harmonic wave generating optical element 31 (i.e., a PPLN crystal), and what emerges from the first second harmonic wave generating optical element 31 is the second harmonic wave of the P polarized light, along with the fundamental wave. The fundamental wave and the second harmonic wave enter a third harmonic wave generating optical element 32 (i.e., an LBO crystal). What emerges from the third harmonic wave generating optical element 32 is the third harmonic wave of the S polarized light, along with the fundamental wave and the second harmonic wave. Furthermore, the first second harmonic wave generating optical element 31 is not limited to a PPLN crystal; for example, a PPKTP crystal, a PPSLT crystal, an LBO crystal, or the like can also be used.

These lights pass through a double wavelength wave plate 33, and thereby only the second harmonic wave is converted to S polarized light. As the double wavelength wave plate 33, for example, a wavelength plate is used that consists of a uniaxial crystalline flat plate that is cut parallel to the optical axis of the crystal. The wavelength plate (i.e., the crystal) is cut such that its thickness is an integer multiple of λ/2 with respect to the light of one wavelength (i.e., the second harmonic wave) and is an integer multiple of λ with respect to the light of an other wavelength so that the polarization of the light of the one wavelength is rotated and the polarization of the light of the other wavelength is not rotated. Furthermore, the second harmonic wave and the third harmonic wave, both of which have become S polarized lights, enter a fifth harmonic wave generating optical element 34 (i.e., an LBO crystal). What emerges from the fifth harmonic wave generating optical element 34 is the fifth harmonic wave of the P polarized light, along with the second harmonic wave and the third harmonic wave. Furthermore, the fundamental wave of the P polarized light transmits through the fifth harmonic wave generating optical element 34 as is.

Because of the effects of walk-off, the cross section of the fifth harmonic wave generated by the fifth harmonic wave generating optical element 34 has an elliptical shape that, if left as is, will degrade convergence and cannot be used in the next wavelength conversion. Accordingly, cylindrical lenses 35, 36 shape the cross section of the elliptical shape into a circular shape. Furthermore, a BBO crystal or a CBO crystal can also be used as the fifth harmonic wave generating optical element 34.

Moreover, the fundamental wave of the P polarized light amplified by the second EDFA 22B enters a second harmonic wave generating optical element 37 (i.e., a PPLN crystal), and what emerges from the second harmonic wave generating optical element 37 is the second harmonic wave of the P polarized light, along with the fundamental wave. Furthermore, a PPKTP crystal, a PPSLT crystal, an LBO crystal, and the like may be used instead of the PPLN crystal.

Furthermore, the fundamental wave of the S polarized light amplified by the third EDFA 22A is combined by a dichroic mirror 41 with the second harmonic wave of the P polarized light discussed above. In this example, the dichroic mirror 41 transmits the fundamental wave and reflects the second harmonic wave. The combined fundamental wave of the S polarized light and second harmonic wave of the P polarized light is combined with the fifth harmonic wave of the P polarized light discussed above by a dichroic mirror 38. In this example, the dichroic mirror 38 transmits the fundamental wave and the second harmonic wave and reflects the fifth harmonic wave. A bulk optical element can be used for combining these lights; for example, a color separating and combining mirror (i.e., a dichroic mirror), a reflective diffractive optical element, a transmissive diffraction optical element, and the like can be used.

The combined fundamental wave of the S polarized light, the second harmonic wave of the P polarized light, and the fifth harmonic wave of the P polarized light enter a seventh harmonic wave generating optical element 39 (i.e., a CLBO crystal), and what emerges from the seventh harmonic wave generating optical element 39 is the seventh harmonic wave of the S polarized light, along with these lights. These lights enter an eighth harmonic wave generating optical element 40 (i.e., a CLBO crystal); here, the fundamental wave of the S polarized light and the seventh harmonic wave of the S polarized light combine, and the eighth harmonic wave of the P polarized light is generated. A dichroic mirror, a polarizing beam splitter, a prism, or the like can be used if one desires to isolate just the eighth harmonic wave with a wavelength of 193.4 nm from the lights of other wavelengths that emerge from the eighth harmonic wave generating optical element 40. In the present embodiment, a dichroic mirror, a polarizing beam splitter, a prism, or the like (not shown) is used to isolate the eighth harmonic wave with a wavelength of 193.4 nm from the lights that emerge from the eighth harmonic wave generating optical element 40, and such is output as the output light of the wavelength converting part 30.

Next, the excitation light source side apparatus 2 will be discussed in detail, referencing FIG. 2. The excitation light source side apparatus 2 comprises: the laser units 61A, 61B, 61C, which supply excitation lights to the optical fibers 4A, 4B, 4C; a central control unit 62; and an interface 63, which receives the monitor signals discussed above via the signal line 5, converts those monitor signals to a prescribed signal format, and supplies such to the central control unit 62.

The laser unit 61A comprises: the Raman fiber laser 71, which serves as an excitation light source; a drive unit 72; a unit control unit 73; and an interlock control unit 74. Under the control of the unit control unit 73, the drive unit 72 supplies a drive electric current to the Raman fiber laser 71, and this drive electric current drives the Raman fiber laser 71. The unit control unit 73 receives from the central control unit 62 an instruction signal that indicates an ON/OFF instruction, which is for either generating or stopping the generation of the excitation light from the Raman fiber laser 71, and, in the case where the excitation light is generated, an excitation light power level instruction; furthermore, the unit control unit 73 controls the drive unit 72 such that the instruction indicated by the instruction signal is implemented. In response to an interlock signal supplied from the central control unit 62, the interlock control unit 74 forcibly stops the generation of the excitation light from the Raman fiber laser 71 by cutting the electrical power supplied from a power supply (not shown) to the drive unit 72. Furthermore, the interlock control unit 74 receives an interlock signal from an emergency stop button and the like (not shown) and forcibly stops the generation of the excitation light from the Raman fiber laser 71. Each of the laser units 61B, 61C has the same configuration as the laser unit 61A, and explanations thereof are therefore omitted.

Based on the monitor signals from the interface 63 (i.e., the monitor signals from the detectors 52A, 52B, 52C of the optical amplifier unit side apparatus 3), the central control unit 62 issues the instruction signal and the interlock signal to each of the laser units 61A, 61B, 61C as explained below.

When the central control unit 62 receives an operation start instruction from a manipulator and the like (not shown), an instruction signal to the effect that excitation light at a prescribed power level WL should be output from the Raman fiber laser 71 is supplied to the unit control unit 73 of each of the laser units 61A, 61B, 61C. As a result, when the output of the excitation light of the Raman fiber laser 71 of each of the laser units 61A, 61B, 61C initially starts, the Raman fiber laser 71 of each of the laser units 61A, 61B, 61C outputs excitation light at the prescribed power level WL. The prescribed power level WL is a low power level at which fiber fusion will not occur even if the connection state of each of the connecting parts 4Ac, 4Bc, 4Cc is poor or if the optical fibers 4Aa, 4Ba, 4Ca and the optical fibers 4Ab, 4Bb, 4Cb are not connected.

Furthermore, when the Raman fiber lasers 71 of the laser units 61A, 61B, 61C output excitation lights at the prescribed power level WL, the central control unit 62 determines, based on the monitor signals supplied from the detectors 52A, 52B, 52C, whether all of the power levels monitored by the detectors 52A, 52B, 52C are at a prescribed value S1 or higher as well as whether one or more of those power levels is less than the prescribed value S1. For the sake of convenience in the explanation, this determination is called the initial determination.

If the initial determination determines that all of the power levels are at the prescribed value S1 or higher, then the central control unit 62 supplies an instruction signal to the unit control units 73 of the laser units 61A, 61B, 61C to the effect that excitation lights with the power level WH (where WH>WL) high enough for the EDFAs 22A, 22B, 22C to perform the desired optical amplification operation should be output to the Raman fiber lasers 71. As a result, excitation lights of the power level WH (where WH WL) generated from the Raman fiber lasers 71 of the laser units 61A, 61B, 61C are supplied to the EDFAs 22A, 22B, 22C, operation transitions to the routine operation state, and thereby the operation of the optical amplifier unit side apparatus 3 explained above outputs output light with a wavelength of 193.4 nm from the wavelength converting part 30. If the monitored power levels are at the prescribed value S1 or higher, then the prescribed value S1 is set to a value that makes it possible to confirm that the optical fibers 4Aa, 4Ba, 4Ca and the optical fibers 4Ab, 4Bb, 4Cb are appropriately connected and that the connection states of the connecting parts 4Ac, 4Bc, 4Cc are satisfactory. Accordingly, after it has been confirmed that the optical fibers 4Aa, 4Ba, 4Ca and the optical fibers 4Ab, 4Bb, 4Cb are appropriately connected and that the connection states of the connecting parts 4Ac, 4Bc, 4Cc are satisfactory, operation transitions to the routine operation state, and therefore there is no risk that fiber fusion will occur once operation has transitioned from the starting state to the routine operation state.

Moreover, if the initial determination determines that any of the power levels is less than the prescribed value S1, then the central control unit 62 transmits an interlock signal to the interlock control units 74 of the laser units 61A, 61B, 61C. As a result, the Raman fiber lasers 71 of the laser units 61A, 61B, 61C stop the output of the excitation lights. At this time, each of the interlock control units 74 not only stops the output of the excitation light of the corresponding Raman fiber laser 71, but preferably also issues an alert by operating an alarm and the like (not shown). If any of the power levels is less than the prescribed value S1, then it is possible that the connection state of any of the connecting parts 4Ac, 4Bc, 4Cc is poor or that any of the optical fibers 4Aa, 4Ba, 4Ca and the optical fibers 4Ab, 4Bb, 4Cb are not connected to one another, respectively. In such a case, operation does not transition to the routine operation state and the Raman fiber lasers 71 of the laser units 61A, 61B, 61C stop the output of the excitation lights, and therefore there is no risk that fiber fusion will occur.

Furthermore, in the present embodiment, as the routine operation state continues (i.e., as the Raman fiber lasers 71 of the laser units 61A, 61B, 61C continue their outputs at a high power level WH), the central control unit 62 repetitively determines, based on the monitor signals supplied from the detectors 52A, 52B, 52C, whether all of the power levels monitored by the detectors 52A, 52B, 52C are greater than or equal to a prescribed value S2, as well as whether any one or more of those power levels is less than the prescribed value S2. For the sake of convenience in the explanation, this determination is called the routine operation in progress determination. Furthermore, in the routine operation state, the power levels of the excitation lights output from the Raman fiber lasers 71 do not necessarily have to be constant.

If the abovementioned routine operation in progress determination determines that all power levels are greater than or equal to the prescribed value S2, then the central control unit 62 causes the routine operation state to continue. If the monitored power levels are greater than or equal to the prescribed value S2, then the prescribed value S2 is set to a value that makes it possible to confirm that the connection states of the connecting parts 4Ac, 4Bc, 4Cc are satisfactory and that the optical fibers 4A, 4B, 4C are undamaged and not broken. Accordingly, because the routine operation state continues while it is confirmed that the connection states of the connecting parts 4Ac, 4Bc, 4Cc are satisfactory and that the optical fibers 4A, 4B, 4C are undamaged and not broken, there is no risk that fiber fusion will occur while the routine operation state is continuing.

Moreover, if the routine operation in progress determination determines that any of the power levels is less than the prescribed value S2, then the central control unit 62 transmits the interlock signal to the interlock control units 74 of the laser units 61A, 61B, 61C. As a result, the Raman fiber lasers 71 of the laser units 61A, 61B, 61C stop the output of the excitation lights. At this time, each of the interlock control units 74 not only stops the output of the excitation light of the corresponding Raman fiber laser 71, but preferably also issues an alert by operating an alarm and the like (not shown). If any of the power levels is less than the prescribed value S2, then it is possible that the connection state of any of the connecting parts 4Ac, 4Bc, 4Cc is in the process of degrading owing to time dependent changes and the like or that the optical fibers 4A, 4B, 4C are damaged or broken. In such a case, the routine operation state ends and the Raman fiber lasers 71 of the laser units 61A, 61B, 61C stop the output of the excitation lights, and therefore there is no risk that fiber fusion will occur.

According to the present embodiment as described above, the likelihood that fiber fusion will occur is greatly reduced.

Furthermore, performing the routine operation in progress determination and the resultant stopping of the output of the excitation lights as in the present embodiment are preferable in order to further reduce the likelihood that fiber fusion will occur. Nevertheless, in the present invention, the routine operation in progress determination and the resultant stopping of the output of the excitation lights do not necessarily have to be performed. Even if the routine operation in progress determination and the resultant stopping of the output of the excitation lights are not performed, the likelihood that fiber fusion will occur can be reduced remarkably compared with the conventional art, as long as the initial determination and the resultant stopping of the output of the excitation lights are performed.

Performing the initial determination and the resultant stopping of the output of the excitation lights are preferable in order to further reduce the likelihood that fiber fusion will occur. Nevertheless, in the present invention, the initial determination and the resultant stopping of the output of the excitation lights do not necessarily have to be performed. Even if the initial determination and the resultant stopping of the output of the excitation lights are not performed, the likelihood that fiber fusion will occur can be reduced remarkably compared with the conventional art, as long as the routine operation in progress determination and the resultant stopping of the output of the excitation lights are performed. In this case, the optical fibers 4A, 4B, 4C may be optical fibers that do not have the connecting parts 4Ac, 4Bc, 4Cc, respectively, along the way.

Second Embodiment

Figure 4:
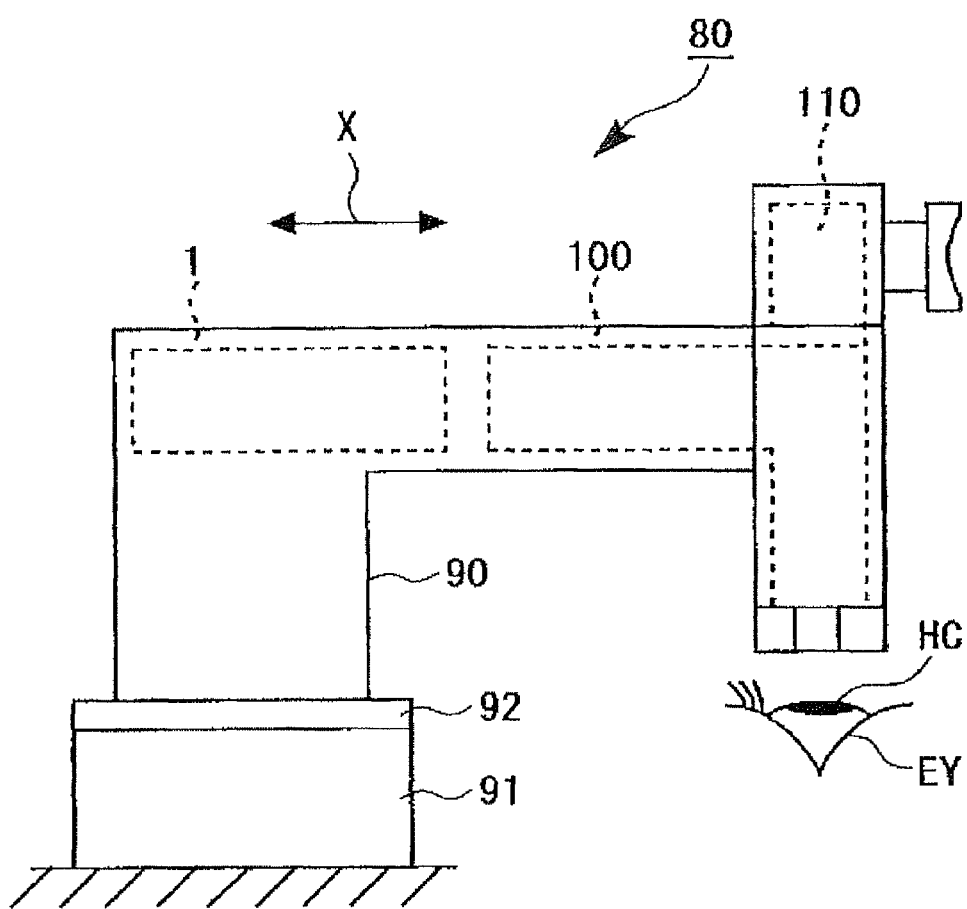
FIG. 4 is a schematic block diagram that shows a light therapy apparatus according to a second embodiment of the present invention.
Figure 5:
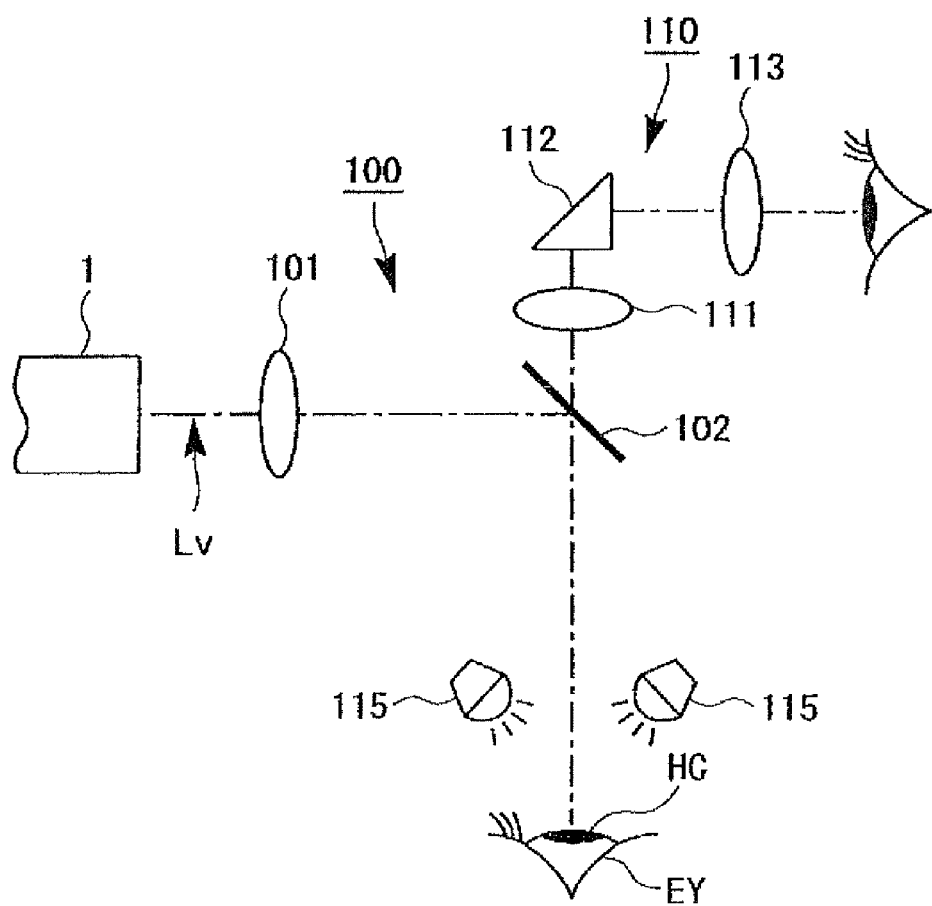
FIG. 5 is a schematic block diagram that shows a radiation optical system and an observation optical system that constitute the light therapy apparatus shown in FIG. 4.

FIG. 4 is a schematic block diagram that shows a light therapy apparatus 80 according to a second embodiment of the present invention. FIG. 5 is a schematic block diagram that shows a radiation optical system 100 and an observation optical system 110, which constitute the light therapy apparatus 80 shown in FIG. 4. The light therapy apparatus 80 according to the present embodiment is an apparatus that comprises and uses the laser apparatus 1 according to the first embodiment to correct cornea curvature or irregularity in order to treat myopia, astigmatism, and the like by radiating ultraviolet laser light (i.e., the output light of the laser apparatus 1) to a cornea and ablating either the corneal surface (i.e., in PRK; photorefractive keratectomy) or the interior of an incised cornea (i.e., in LASIK; laser intrastromal keratomileusis).

As shown in FIG. 4, the light therapy apparatus 80 basically comprises, inside an apparatus casing 90, the laser apparatus 1 discussed above; the radiation optical system 100, which guides and radiates ultraviolet laser light Lv output from the laser apparatus 1 to a surface (i.e., a therapy region) of a cornea HC of an eyeball EY; and the observation optical system 110, which observes the therapy region.

The apparatus casing 90 is provided and disposed on a base part 91 with an XY motion table 92 interposed therebetween; furthermore, the entire apparatus casing 90 is configured moveably with respect to the eyeball EY in the arrow X directions in FIG. 4, namely, in the lateral directions in the drawing, as well as in the Y directions perpendicular to the paper surface.

FIG. 5 shows the configuration of the radiation optical system 100 and the observation optical system 110. The radiation optical system 100 comprises: a condenser lens 101, which condenses the ultraviolet laser light Lv with a wavelength of 193.4 nm emitted from the laser apparatus 1 such that it forms a prescribed spot diameter on the eyeball EY; and a dichroic mirror 102, which reflects the ultraviolet laser light from the condenser lens 101 and radiates such to the surface of the cornea HC of the eyeball EY, namely, the therapy target. The dichroic mirror 102 is set such that it reflects light in the ultraviolet region and transmits light in the visible region; furthermore, the dichroic mirror 102 can reflect the ultraviolet laser light Lv coaxially with the optical axis of the observation optical system 110 and can radiate such to the surface of the cornea HC.

Moreover, the observation optical system 110 comprises: illumination lamps 115 that illuminate the surface of the cornea HC of the eyeball EY, which constitutes the therapy target; an objective 111, which receives light in the visible region that was radiated by the illumination lamps 115, reflected by the cornea HC, and transmitted through the dichroic mirror 102; a prism 112, which reflects the light from the objective 111; and an eyepiece 113, which receives the reflected light from the prism 112 and forms an image; furthermore, the observation optical system 110 is configured such that an enlarged image of the cornea HC from the light that passes through the eyepiece 113 can be observed.

Thereby, a specialist, such as an ophthalmologist, can perform light therapy while visually observing the therapy target via the observation optical system 110. For example, while the eyeball EY is being visually observed, the apparatus casing 90 is moved in the X directions and the Y directions, the ultraviolet laser light is radiated as a spot light to the surface of the cornea HC, which is the therapy target, and thereby the radiated area is ablated. In addition, corrective therapy, such as the correction of myopia, astigmatism, and farsightedness, can be performed by using an operation control apparatus (not shown) to control the operation of the XY motion table 92, moving the apparatus casing 90 in the X directions and the Y directions, scanning the surface of the cornea HC with the radiated spot light, and thereby ablating the corneal surface.

The light therapy apparatus according to the present embodiment uses the laser apparatus 1 according to the first embodiment, which makes it possible to reduce the likelihood that fiber fusion will occur.

Third Embodiment

Figure 6:
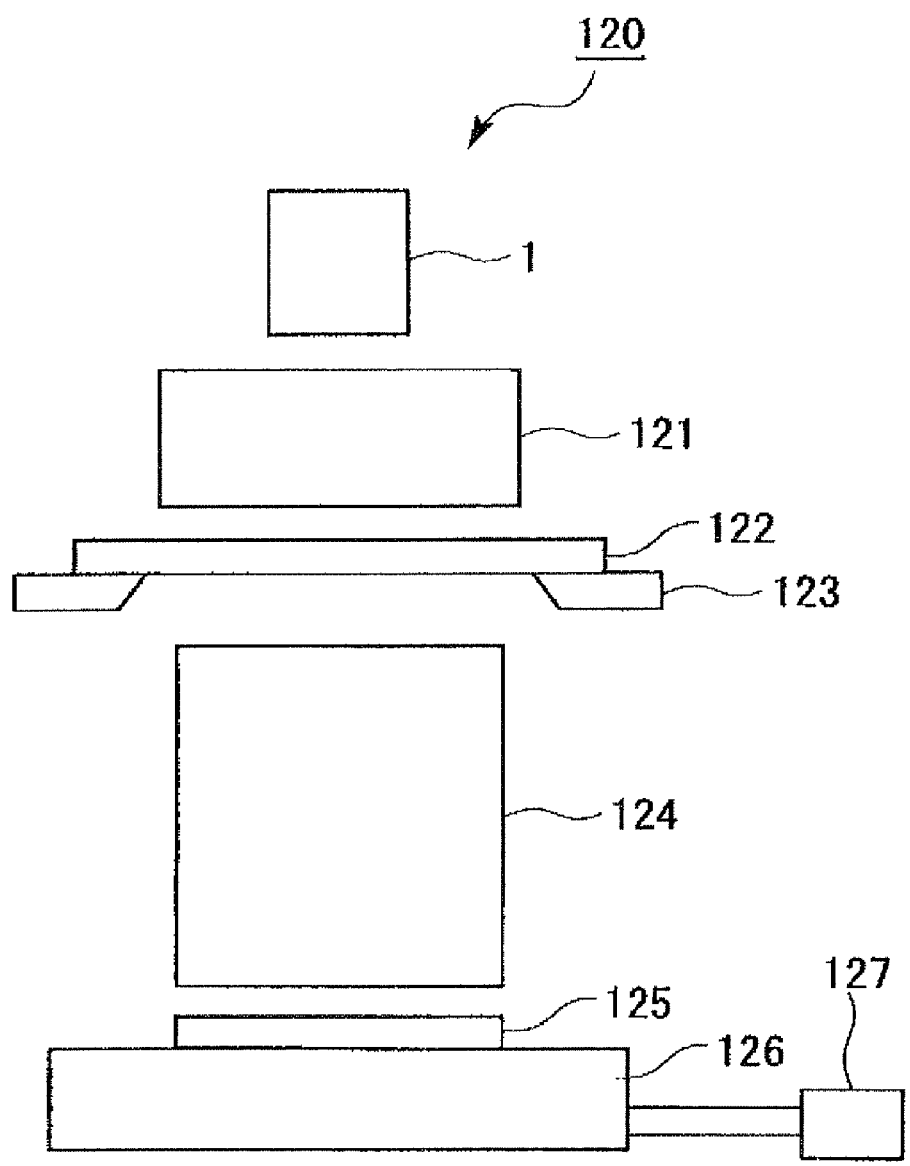
FIG. 6 is a schematic block diagram that schematically shows an exposure apparatus according to a third embodiment of the present embodiment.

FIG. 6 is a schematic block diagram that schematically shows an exposure apparatus 120 according to a third embodiment of the present invention. The exposure apparatus 120 according to the present embodiment uses the laser apparatus 1 according to the first embodiment and is used by a photolithographic process, which is one of the semiconductor manufacturing processes. An exposure apparatus that is used in a photolithographic process operates on the same principle as that of photoengraving; namely, a device pattern that is precisely drawn on a photomask (i.e., a reticle) is optically projected and transferred to a semiconductor wafer, a glass substrate, and the like, which is coated with a photoresist.

The exposure apparatus 120 according to the present embodiment comprises: the laser apparatus 1 discussed above; a radiation optical system 121 (i.e., an illumination optical system); a mask support platform 123, which supports a photomask 122; a projection optical system 124; a mounting platform 126 whereon a semiconductor wafer 125, which is a photosensitive object and constitutes an exposure target, is mounted and held; and a drive apparatus 127, which moves the mounting platform 126 horizontally.

In the exposure apparatus 120, the output light output from the laser apparatus 1 discussed above enters the radiation optical system 121, which comprises a plurality of lenses, passes therethrough, and then irradiates the entire surface of the photomask 122, which is supported by the mask support platform 123. In the present embodiment, the laser apparatus 1 and the radiation optical system 121 constitute a light radiating apparatus that irradiates the photomask 122, which is the target. The light radiated in this manner and that passes through the photomask 122 contains an image of the device pattern drawn on the photomask 122, and this light transits the projection optical system 124 and is radiated to a prescribed position of the semiconductor wafer 125, which is mounted on the mounting platform 126. At this time, the image of the device pattern of the photomask 122 produced by the projection optical system 124 is reduced and formed on the semiconductor wafer 125, thereby exposing the semiconductor wafer 125.

The exposure apparatus 120 according to the present embodiment uses the laser apparatus 1 according to the first embodiment, which makes it possible to reduce the likelihood that fiber fusion will occur.

In the device manufacturing method according to one embodiment of the present invention, a semiconductor device is manufactured by: a process that designs the functions and performance of the device; a process that forms a wafer from silicon material; a lithographic process, including a process that uses the exposure apparatus 120 according to the third embodiment to expose the semiconductor wafer 125 via the photomask 122; a process that forms a circuit pattern by, for example, etching; a device assembling process (which includes a dicing process, a bonding process, and a packaging process); and an inspecting process. Furthermore, the present invention is not limited to an exposure apparatus for fabricating semiconductor devices and can also be adapted to exposure apparatuses for fabricating various other devices.

Fourth Embodiment

Figure 7:
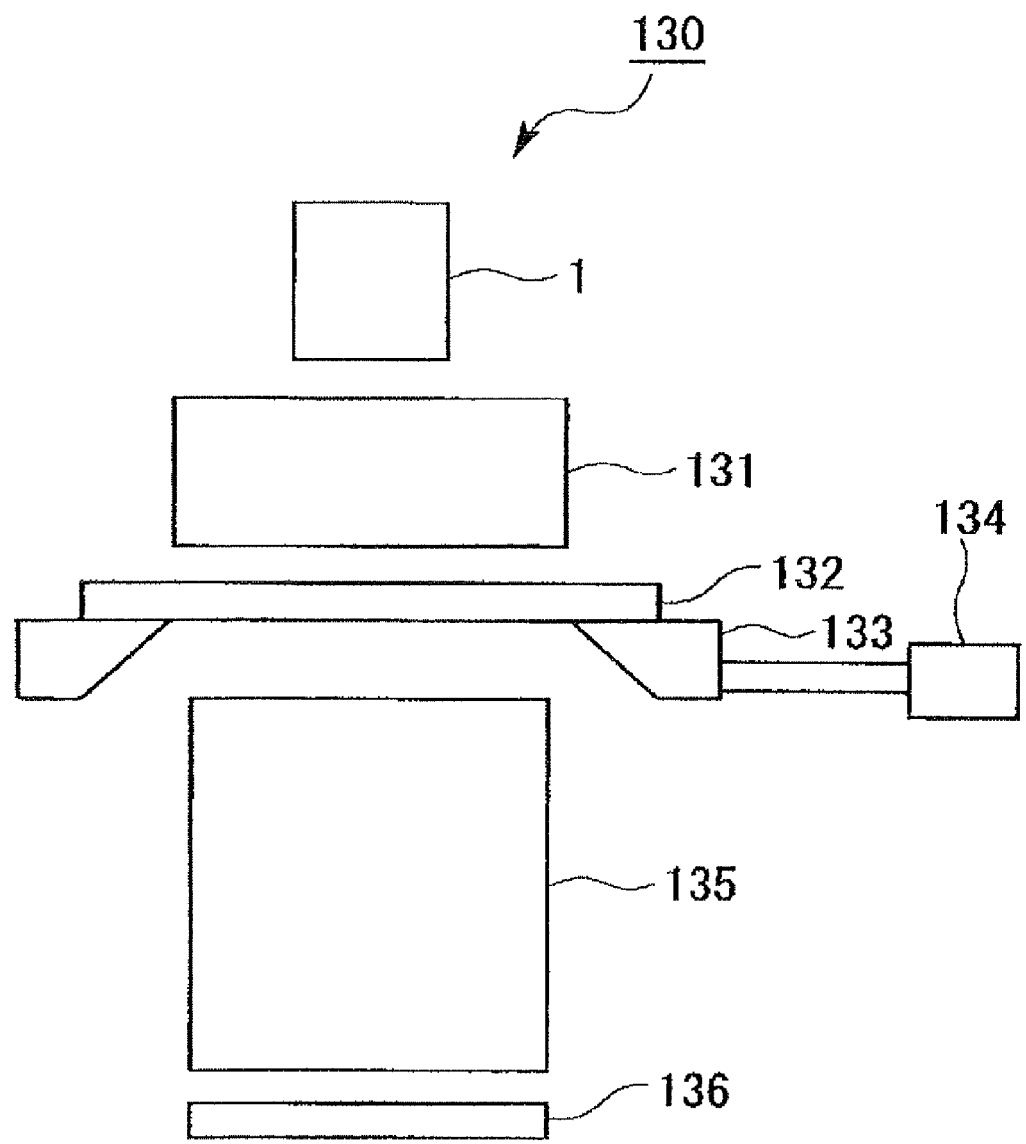
FIG. 7 is a schematic block diagram that shows a mask defect inspection apparatus according to a fourth embodiment of the present invention.

FIG. 7 is a schematic block diagram that shows a mask defect inspection apparatus 130, which serves as an object inspection apparatus, according to a fourth embodiment of the present invention.

In the mask defect inspection apparatus 130 according to the present embodiment, a device pattern, which is precisely drawn on a photomask 132, is optically projected onto a TDI (time delay and integration) sensor 136, the sensor image and a prescribed reference image are compared, and any defects in the pattern are identified based on differences between those images.

The mask defect inspection apparatus 130 comprises: the laser apparatus 1 according to the first embodiment; an illumination optical system 131; a mask support platform 133, which supports the photomask 132; a drive apparatus 134, which moves the mask support platform 133 horizontally; a projection optical system 135; and the TDI sensor 136.

In the mask defect inspection apparatus 130, the output light output from the laser apparatus 1 discussed above enters the illumination optical system 131, which comprises a plurality of lenses, passes therethrough, and is radiated to a prescribed area of the photomask 132, which is supported by the mask support platform 133. The light that is radiated in this manner and that passes through the photomask 132 contains an image of the device pattern drawn on the photomask 132; furthermore, this light transits the projection optical system 135 and forms an image at a prescribed position of the TDI sensor 136. Furthermore, the horizontal movement speed of the mask support platform 133 is synchronized to a transfer clock of the TDI sensor 136.

The mask defect inspection apparatus 130 according to the present embodiment uses the laser apparatus 1 according to the first embodiment, which makes it possible to reduce the likelihood that fiber fusion will occur.

The text above explained the embodiments of the present invention, but the present invention is not limited to these embodiments.

For example, in the first embodiment, some other rare earth doped fiber resonator or fiber amplifier may be used for each of the EDFAs 22A, 22B, 22C. In addition, a semiconductor laser, such as an Er-YAG laser, may be used as each of the excitation light sources instead of the Raman fiber lasers 71. Furthermore, it is obvious that the wavelength of the output light output from the laser apparatus 1 is not limited to 193.4 nm. In addition, the second through fourth embodiments were offered merely as examples of apparatuses that use the laser apparatus 1 according to the present invention, and the laser apparatus 1 according to the present invention can be adapted to various other types of apparatuses.

EXPLANATION OF SYMBOLS

1 Laser apparatus
2 Excitation light source side apparatus
3 Optical amplifier unit side apparatus
4A, 4B, 4C, 4Aa, 4Ba, 4Ca, 4Ab, 4Bb, 4Cb Optical fibers
4Ac, 4Bc, 4Cc Connecting parts
61A, 61B, 61C Laser units
62 Central control unit
52A, 52B, 52C Detectors (monitor units)
20 Optical amplifier unit
30 Wavelength converting part
80 Light therapy apparatus
120 Exposure apparatus
130 Mask defect inspection apparatus

The invention claimed is:

1. A laser apparatus that includes an excitation light source, a laser light source, and an optical amplifier unit that optically amplifies a laser light generated by the laser light source by means of excitation light that is output from the excitation light source, the excitation light being transmitted to the optical amplifier unit through an optical fiber, and amplified laser light being output from the optical amplifier unit, the laser apparatus comprising:
   a control unit that controls the excitation light source;
   a monitor unit that monitors a power level of the excitation light transmitted from the excitation light source to the optical amplifier unit through the optical fiber; and
   a connecting part that is configured to connect and disconnect the optical fiber; wherein:
   the control unit controls the excitation light source such that:
      (i) at an initial stage of outputting the excitation light from the excitation light source, an excitation light power being output is lower than a regular excitation light power required by the optical amplifier unit to make a regular amplified laser power,
      (ii) when the power level of the excitation light monitored by the monitor unit during the initial stage of outputting the excitation light is greater than or equal to a prescribed value, the control unit controls the excitation light source such that the excitation light having the regular excitation light power is output, and
      (iii) when the power level of the excitation light monitored by the monitor unit during the initial stage of outputting the excitation light is less than the prescribed value, the control unit controls the excitation light source to stop the output of the excitation light.

2. The laser apparatus according to claim 1, wherein when the excitation light source is outputting the excitation light at the regular excitation light power, the control unit controls the excitation light source such that the output of the excitation light by the excitation light source is stopped if the power level monitored by the monitor unit is less than the prescribed value.

3. The laser apparatus according to claim 1, further comprising:
   a wavelength converting part that converts the amplified laser light output from the optical amplifier unit to a light of a prescribed wavelength; wherein
   the light of the prescribed wavelength output from the wavelength converting part is output as an output light.

4. A light therapy apparatus, comprising:
   the laser apparatus according to claim 1; and
   a radiation optical system that guides and radiates an output light output from the laser apparatus to a therapy region.

5. An exposure apparatus, which transfers a pattern of a mask to a photosensitive object, the exposure apparatus comprising:
   the laser apparatus according to claim 1;
   an illumination optical system that radiates an output light output from the laser apparatus to the mask; and
   a projection optical system that projects a light from the mask to the photosensitive object.

6. A device manufacturing method, which includes a lithographic process, wherein
   the lithographic process uses the exposure apparatus according to claim 5 to transfer a pattern of the mask to the photosensitive object.

7. An object inspection apparatus, comprising:
the laser apparatus according to claim 1;
a support part that supports an object to be inspected;
a detector that detects a projected image of the object to be inspected;
an illumination optical system that radiates an output light output from the laser apparatus to the object to be inspected; and
a projection optical system, which projects light from the object to be inspected to the detector.

8. The laser apparatus according to claim 1, wherein the excitation light source and the optical amplifier unit can be separated from each other or connected to each other by the connecting part.

* * * * *